United States Patent [19]

Latter et al.

[11] Patent Number: 5,053,418
[45] Date of Patent: Oct. 1, 1991

[54] ANTIPROTOZOAL AGENTS

[75] Inventors: Victoria S. Latter; Alan T. Hudson, both of Kent; William H. G. Richards, Herts; Anthony W. Randall, Kent, all of United Kingdom

[73] Assignee: Burroughs Wellcome Co., Research Triangle Park, N.C.

[21] Appl. No.: 449,485

[22] Filed: Dec. 11, 1989

Related U.S. Application Data

[63] Continuation of Ser. No. 769,797, Aug. 26, 1985, abandoned, which is a continuation of Ser. No. 599,331, Apr. 12, 1984, abandoned.

[30] Foreign Application Priority Data

Apr. 14, 1983 [GB] United Kingdom ............... 8310140

[51] Int. Cl.$^5$ ............................................. A61K 31/44
[52] U.S. Cl. .................................... 514/345; 514/682
[58] Field of Search ............................... 514/345, 682

[56] References Cited

U.S. PATENT DOCUMENTS

| 2,553,648 | 5/1951 | Fieser et al. | 260/396 |
| 3,206,358 | 9/1965 | Stevenson | 167/53 |
| 3,347,742 | 10/1967 | Rogers | 167/53.2 |
| 3,367,830 | 2/1968 | Sarett | 167/53.1 |

FOREIGN PATENT DOCUMENTS

| 0077551 | 4/1983 | European Pat. Off. |
| 0002228 | 2/1984 | European Pat. Off. |
| 0077550 | 7/1985 | European Pat. Off. |
| 2641343 | 4/1977 | Fed. Rep. of Germany |
| 1553424 | 9/1979 | United Kingdom |

OTHER PUBLICATIONS

Fieser, et al., Journal of Medicinal Chemistry, vol. 10, No. 1, Jun. 26, 1967, Naphthoquinone Antimalarials, XXIX, 2-Hydroxy-3-(w-cyclohexylalkyl)-1,4-naphthoquinones, pp. 513–517.

Fieser et al., vol. 70, pp. 3158–3164, Naphthoquinone Antimalarials II, Correlation of Structure and Activity Against P. Lophurae in Ducks[1].

Challey et al., "Synergism Between 4-Hydroxyquinoline and Pyridone Cocidiostats", The Journal of Parasitology 59(3):502–504 (1973).

Fry et al., "Effects of Decoquinate and Clopidol on Electron Transport in Mitochondria of Eimeria Tenella", Biochemical Pharmacology, 33(2):229–240 (1984).

Wang, "Studies of the Mitochondria from Eimeria Tennella and Inhibition of the Electron Transport by Quinolone Coceidiostats", Biochimica et Biophysica Acta, 396, pp. 210–219 (1975).

Wang, "Biochemistry and Physiology of Coceidia", pp. 197–198 (1975).

Wang, "Biochemical and Nutritional Aspects of Coccidia", Avian Coccidiosis, British Poultry Science Ltd., pp. 135–184 (1978).

Primary Examiner—Frederick E. Waddell
Assistant Examiner—Russell Travers
Attorney, Agent, or Firm—Donald Brown

[57] ABSTRACT

Novel combinations of an antiprotozoal naphthoquinone and a 4-pyridinol or an alkanoic ester thereof wherein the antiprotozoal activity of the combination is potentiated with respect to the corresponding activity of the components of the combination. The combinations are especially useful for the treatment or porphylaxis of malaria.

2 Claims, No Drawings

ANTIPROTOZOAL AGENTS

This is a continuation of copending application Ser. No. 06/769,797 filed on Aug. 26, 1985 now abandoned which is a continuation of application Ser. No. 599,331, filed Apr. 12, 1984, now abandoned.

The present invention relates to combinations of naphthoquinones and pyridine derivatives. More specifically it is concerned with potentiating combinations of anti-protozoal naphthoquinones and 4-pyridinol derivatives.

Naphthoquinones of diverse structures have been described as possessing useful antiprotozoal activity, for example antimalarial, anticoccidial and antitheilerial activity. Some of these compounds have also been described as possessing activity against external parasites.

Fieser et al, J. Amer. Chem. Soc. 1948, 70, 3158–3164 (and references cited therein) describes a large number of 2-substituted-3-hydroxy-1, 4-naphthoquinones as having antimalarial activity. A number of these compounds have also been described in U.S. Pat. No. 2,553,648.

U.S. Pat. No. 3,367,830 describes a series of 2-substituted-3-hydroxy-1, 4-naphthoquinones as anticoccidial agents.

U.S. Pat. No. 3,347,742 describes the use of 2-(4'-cyclohexylcyclohexyl)-3-hydroxy-1,4-naphthoquinone as an anticoccidial agent.

U.K. Patent Specification No. 1553424 describes the use of 2-cyclohexyl- and 2-cyclohexylalkyl-3-hydroxy-1,4-naphthoquinones as antitheilerial agents.

European Patent Specification No. 0 002 228 describes a number of 2-cycloalkyl-3-hydroxy-1,4-naphthoquinones as antitheilerial agents.

European Patent Specification 77551 describes a series of 2-(4-substituted cyclohexyl)-3-hydroxy-1,4-naphthoquinones as antimalarial and anticoccidial agents.

European Patent Specification 77550 describes a series of 2-(4-substituted cyclohexylmethyl)-3-hydroxy-1,4-naphthoquinones as antitheilerial agents.

German Offenlegungsschrift 2,641,343 describes a series of 2-higher alkyl-3-hydroxy-1,4-naphthoquinones having acaricidal and aphicidal activity.

A number of pyridinol derivatives have also been described in the literature as having antiprotozoal activity. Thus, for example, U.S. Pat. No. 3,206,358 describes a series of 2,6-dialkyl-3,5-dihalo-4-hydroxypyridines having anticoccidial activity.

It has now been found that potentiation of antiprotozoal activity is achieved by combining an antiprotozoal naphthoquinone and a 4-pyridinol or an alkanoic ester thereof.

The invention therefore provides, in a first aspect, a combination of an antiprotozoal naphthoquinone and a 4-pyridinol, or an alkanoic ester thereof, wherein the naphthoquinone and 4-pyridinol, or alkanoic ester thereof, are present in a potentiating ratio.

The term 'potentiating ratio' is used herein to indicate that the naphthoquinone and 4-pyridinol, or alkanoic esters thereof, are present in a ratio such that the antiprotozoal activity of the combination is greater than that of either the naphthoquinone or the 4-pyridinol, or alkanoic ester thereof, alone or of the merely additive activity of the combination based upon the activities of the individual components.

The naphthoquinone may comprise any naphthoquinone known or found to possess anti-protozoal activity.

Particularly preferred naphthoquinones are 1,4-naphthoquinones of the general formula (I)

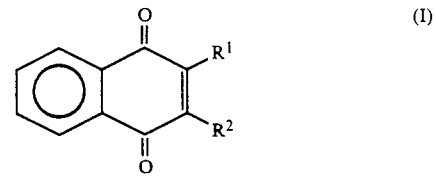

wherein $R^1$ is an aliphatic hydrocarbon residue such as a straight or branched chain alkyl group, in particular containing from 1 to 14 carbon atoms, a cycloalkyl group in particular containing from 3 to 8 carbon atoms, or a cycloalkylalkyl group in particular where the cycloalkyl moiety has from 3 to 8 carbon atoms and the alkyl moiety has 1 to 8 carbon atoms, and such groups being optionally substituted by one or more substituents selected from $C_{1-6}$ alkyl (including cycloalkyl), $C_{1-6}$ alkoxy, phenyl and hydroxy; $R^2$ is hydroxy, $C_{1-4}$ acyl, $C_{1-6}$ alkoxy, hydrogen or halogen.

Preferred compounds of formula (I) include those wherein the group $R^1$ comprises or contains a cyclohexyl moiety, particularly those wherein $R^1$ is a 4-substituted cyclohexyl group, especially a 4-t-butylcyclohexyl group.

Specific compounds of formula (I) include for example:
2-(4-t-butylcyclohexyl)-3-hydroxy-1,4-naphthoquinone,
2-(4-t-pentylcyclohexyl)-3-hydroxy-1,4-naphthoquinone,
2-(4-t-butylcyclohexylmethyl)-3-hydroxy-1,4-naphthoquinone,
2-cyclohexyl-3-hydroxy-1,4-naphthoquinone,
2-(4-phenylcyclohexyl)-3-hydroxy-1,4-naphthoquinone,
2-(8-cyclohexyloctyl)-3-hydroxy-1,4-naphthoquinone,
2-(4-cyclohexylcyclohexyl)-3-hydroxy-1,4-naphthoquinone,
2-(3-cyclohexylpropyl)-3-hydroxy-1,4-naphthoquinone,
2-(4-t-butoxycyclohexyl)-3-hydroxy-1,4-naphthoquinone,
2-n-nonyl-3-hydroxy-1,4-naphthoquinone,
2-(4,4-dimethylcyclohexyl)-3-hydroxy-1,4-naphthoquinone,
2-acetoxy-3-(4,4-dimethylcyclohexyl)-1,4-naphthoquinone,
2-acetoxy-3-cyclohexyl-1,4-naphthoquinone,
2-(3-t-butylcyclohexyl)-3-hydroxy-1,4-naphthoquinone,
2-cyclopentyl-3-hydroxy-1,4-naphthoquinone, and
2-(4-(4'-chlorophenyl)cyclohexyl)-3-hydroxy-1,4-naphthoquinone.

Other naphthoquinones which may be employed in the combinations according to the invention are described in the literature, for example:
J. Amer. Chem. Soc. 1948, 70, 3158–3164;
U.S. Pat. No. 2,553,648
U.S. Pat. No. 3,367,830
U.S. Pat. No. 3,347,742
J. Med. Chem 1967, 10, 513
UK Patent Specification No. 1 553 424
European Patent Specification No. 0 002 228
European Patent Specification No. 77550
European Patent Specification No. 77551
German Offenlegungsschrift 2,641,343

The above references, and the naphthoquinones disclosed therein, are incorporated herein by reference.

The pyridinols which may be employed in the combinations of the invention include those described in U.S. Pat. No. 3,206,358 which is incorporated herein by reference.

Preferred pyridinols include those of formula (II)

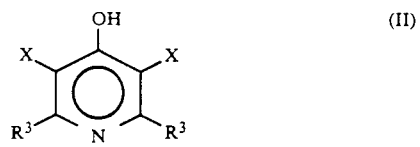

wherein each $R^3$ is the same or different and is an alkyl group, in particular a $C_{1-4}$ alkyl group and each X is the same or different and is halogen and $C_{1-6}$ alkanoic acid esters thereof.

Particularly preferred compounds of formula (II) include
3,5-dichloro-2,6-dimethyl-4-pyridinol;
3,5-dibromo-2,6-dimethyl-4-pyridinol;
3,5-dichloro-2,6-dipropyl-4-pyridinol and
3,5-dibromo-2,6-dipropyl-4-pyridinol.

The naphthoquinones and 4-pyridinols and alkanoic esters thereof employed in the combinations according to the invention may be prepared in conventional manner, for example, using analogous techniques to those described in the above-mentioned references.

The two active ingredients of the combinations of the invention may be present in any convenient potentiating ratio. The actual ratio will vary depending primarily upon the inherent antiprotozoal activity of the naphthoquinone. Thus the more active the naphthoquinone the greater will be the ratio of pyridinol to naphthoquinone. However, in general, the ratio of naphthoquinone to pyridinol (w/w) will be in the range of 1:500 to 1:1. The ratio of more active naphthoquinones to pyridinol is advantageously about 1:50 to 1:500 or even greater; for less active naphthoquinones the ratio will be lower, for example in the ranges of about 1:10 to 1:100 or 1:1 to 1:25 depending upon the activity of the naphthoquinone.

According to a further feature of the invention we provide a combination as described herein for use as a therapeutic agent, for example for use in the treatment or prophylaxis of a protozoal disease as described below.

According to a further feature of the present invention we provide a method for the treatment or prophylaxis of a protozoal disease in a host which comprises administering to the host an antiprotozoal amount of a combination as hereinbefore defined.

Examples of protozoal diseases which may be treated in accordance with the invention include coccidiosis and malarial infections, in hosts, including mammals (such as man in the case of malaria) and birds (such as poultry in the case of coccidiosis).

The amount of naphthoquinone required for therapeutic effect is at the ultimate discretion of the physician/veterinarian carrying out the treatment and will, of course, vary not only with the nature of the infection to be treated but also with the particular naphthoquinone and pyridinol used and the ratio thereof. In general, however, a suitable daily dose for a mammal (including man) for the treatment of malaria, for example, will lie in the range of 0.1 mg to 200 mg/kg bodyweight, for example 1 mg to 100 mg/kg such as 10 mg to 40 mg/kg.

The amount of pyridinol present in the combination will be that necessary to provide the appropriate potentiating ratio of naphthoquinone to pyridinol as hereinbefore defined. Thus the amount of pyridinol will vary according to the particular naphthoquinone employed but will be apparent to someone skilled in the art.

It will be appreciated that the amount of the combinations, according to the invention, required for use in treatment or prophylaxis will vary not only with the active compound but also with the route of administration and nature of the infection. In general a suitable dose for a mammal (including man) for treatment, for example of malaria, will lie in the range of 0.1 mg to 200 mg per kilogram bodyweight per day, with a preferred range of 1 mg to 100 mg, particularly 10 to 40 mg. For the prophylaxis or treatment of coccidiosis the compound will normally be administered ad lib in drinking water or diet and suitable levels of drug will be in the range of 1 to 500 ppm, preferably 10–400 ppm ideally about 200 ppm.

The combinations of the invention are preferably employed as antiprotozoal agents in the form of therapeutic (pharmaceutical or veterinary) formulations.

According to a further feature of the present invention we provide a therapeutic formulation comprising a combination, according to the invention, together with one or more pharmaceutically acceptable carriers therefore and/or optionally one or more further therapeutic and/or prophylactic ingredients. The combination according to the invention is present in the therapeutic formulations in an effective antiprotozoal amount.

The combinations may conveniently be presented (as therapeutic formulations) in unit dosage form. A convenient unit dose formulation contains the combination in an amount of from 10 mg to 1 g.

Therapeutic formulations include those suitable for oral, rectal or parenteral (including intramuscular and intravenous) administration, although the oral route is preferred. The formulations may, where appropriate, be conveniently presented in discrete dosage units and may be prepared by any of the methods well known in the art of pharmacy. All methods include the step of bringing into association the active compound with liquid carriers or finely divided solid carriers of both and then, if necessary, shaping the product into the desired formulation.

Therapeutic formulations suitable for oral administration wherein the carrier is a solid are most preferably presented as unit dose formulations such as boluses, capsules, cachets or tablets each containing a predetermined amount of the combination. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may be optionally scored. Capsules may be prepared by filling the combination, either alone or in admixture with one or more accessory ingredients, into the capsule cases and then sealing them in the usual manner. Cachets are analogous to capsules wherein the combination together with any accessory ingredient(s) is sealed in a rice paper envelope. Therapeutic formulations suitable for oral administration wherein the carrier is a liquid may be presented as a solution or a suspension in an aqueous liquid or a non-aqueous liquid, or as an oil-in-water or water-in-oil liquid emulsion.

Therapeutic formulations suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

Therapeutic formulations suitable for parenteral administration include sterile solutions or suspensions of the combination in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface-active agents, thickeners, lubricants, preservatives (including anti-oxidants) and the like, and substances included for the purpose of rendering the formulation isotonic with the blood of the intended recipient.

The therapeutic formulations for veterinary use, may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The following examples illustrate the invention:

EXAMPLE 1

In vitro activity of combinations of 2-(4-t-butylcyclohexyl)-3-chloro-1,4-naphthoquinone and 3,5-dichloro-2,6-dimethylpyridinol against P.falciparum The effect of combinations of 2-(4-t-butylcyclohexyl)-3-chloro-1,4-naphthoquinone and 3,5-dichloro-2,6-dimethylpyridinol ("naphthoquinone/4-pyridinol combinations") against *P.falciparum* were determined and compared to the effect of each drug alone by a modification of the method of Desjardins et al (Antimicrobial Agents and Chemotherapy 16, 710–718 (1979)). Each of the two compounds to be tested were dissolved in ethanol at a concentration of 10 mg/L and serially diluted with RPMI 1640 medium and 10% (v/v) human plasma in microtitration plates. *P.falciparum*-parasitised and fresh blood cells were added together with $^3$H-adenosine or $^3$H-hypoxanthine in RPMI 1640 medium and 10% human plasma. The cultures were then incubated at 37° C. for 43 hours, harvested and the particulate contents collected on glass fibre filter papers which were washed copiously with water using a Cooke Microtiter System (Dynatech Labs. Europe); the filter papers were dried and the radioactivity measured using a scintillation counter. Infected, untreated and uninfected cultures were included as controls. Percent inhibition was correlated with dose to provide an IC$_{50}$ for each drug alone.

For subsequent combination experiments the individual drug solutions and mixtures thereof were serially diluted. The percentage inhibition of incorporation of radio-activity in the drug-treated cultures for a range of concentrations and combinations thereof were determined and are shown in Table 1.

The IC$_{50}$ of each drug at a fixed concentration of the other was determined by linear regression and is shown in Table II. Plotting of these values on an isobologram demonstrated that the anti-malarial activity of the drugs in combination was greater than that of the predicted additive effect of the individual components.

TABLE I

| Concentration of naphthoquinone in mg/L | Concentration of (4-pyridinol) in mg/L | | | | | | | | | | |
|---|---|---|---|---|---|---|---|---|---|---|---|
| | 0 | 6.4 | 3.2 | 1.6 | 0.80 | 0.40 | 0.20 | 0.10 | 0.050 | 0.025 | 0.0125 | 0.0063 |
| 0.0 | 0 | | 74 | 55 | 44 | 22 | 18 | 24 | | | | |
| 4.0 | | | | | | 84 | 83 | 80 | | | | |
| 2.0 | 75 | | | | 77 | 81 | 78 | 75 | 70 | | | |
| 1.0 | 55 | | | 81 | 81 | 74 | 70 | 70 | 57 | 56 | | |
| 0.50 | 31 | | 78 | 78 | 78 | 74 | 62 | 60 | 49 | 47 | 30 | |
| 0.25 | 17 | 79 | 74 | 74 | 66 | 60 | 68 | 56 | 37 | 47 | 31 | 23 |
| 0.125 | 14 | 83 | 70 | 60 | 57 | 47 | 34 | 47 | 43 | 41 | 8 | 6 |
| 0.0625 | 18 | | 64 | 58 | 47 | 29 | 36 | 23 | 37 | 14 | 25 | |
| 0.03125 | | | | 50 | 33 | 29 | 25 | 18 | 11 | 3 | | |
| 0.0156 | | | | | 27 | 26 | 32 | 37 | 2 | | | |
| 0.0078 | | | | | | 32 | 23 | 32 | | | | |
| 0.0039 | | | | | | | 27 | | | | | |

TABLE II

| Fixed concentration of clopidol (4-pyridinol) in mg/L | ED$_{50}$ for naphthoquinone in mg/L | | Fixed concentration of naphthoquinine in mg/L | ED$_{50}$ for Clopidol (4-pyridinol) in mg/L | |
|---|---|---|---|---|---|
| 0.000 | 0.851 | (2.18 to 0.464) | 0.0 | 1.18 | (1.44 to 0.980) |
| 0.00625 | 0.699 | (none) | 0.00781 | 1.63 | (none) |

TABLE II-continued

| Fixed concentration of clopidol (4-pyridinol) in mg/L | ED$_{50}$ for naphthoquinone in mg/L | | Fixed concentration of naphthoquinine in mg/L | ED$_{50}$ for Clopidol (4-pyridinol) in mg/L | |
|---|---|---|---|---|---|
| 0.0125 | 0.401 | (3.03 to 0.271) | 0.0156 | 0.128 | (none) |
| 0.0250 | 0.478 | (1.41 to 0.271) | 0.0313 | 2.57 | (647000 to 0.721) |
| 0.0500 | 0.447 | (0.766 to 0.295) | 0.0625 | 1.03 | (14.2 to 0.405) |
| 0.100 | 0.287 | (0.510 to 0.128) | 0.125 | 0.578 | (1.52 to 0.0224) |
| 0.200 | 0.198 | (0.381 to 0.082) | 0.250 | 0.074 | (0.183 to 0.00955) |
| 0.400 | 0.155 | (1.31 to 0.000) | 0.500 | 0.052 | (0.081 to 0.289) |
| 0.800 | 0.0801 | (0.225 to 0.0239) | 1.00 | 0.0092 | (0.039 to 0.000013) |
| 1.60 | 0.0303 | (0.0780 to 0.00075) | 2.00 | 0.00097 | (none) |
| 3.20 | 0.0075 | (0.039 to 0.0000) | 4.00 | 0.00012 | (none) |

EXAMPLE 2

Effect of 4-pyridinol/naphthoquinone combinations on P.falciparum

By the method of Example 1 the effect of a number of naphthoquinone/clopidol (4-pyridinol) combinations on P.falciparum in vitro were determined. Results, expressed as % inhibition of radioactivity incorporation, are given in Table III.

TABLE III

Naphthoquinone alone $$\begin{array}{c}\text{structure with } R^1, R^2 \text{ on naphthoquinone}\end{array}$$

| (a) R$^1$ (b) R$^2$ | Concentration in mg/L | % Inhibition | Clopidol (4-pyridinol) alone Concentration in mg/L | % Inhibition | Naphthoquinone + Clopidol (4-pyridinol) % Inhibition |
|---|---|---|---|---|---|
| (a) 4-ethylcyclohexyl  | 0.0000125 | 51 | 0.400 | 12 | 86 |
| | 0.0000125 | 51 | 0.200 | 17 | 73 |
| (b) OH | 0.00000625 | 31 | 0.400 | 12 | 47 |
| | 0.00000625 | 31 | 0.200 | 17 | 48 |
| (a) 4,4-dimethylcyclohexyl 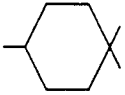 | 0.00150 | 0 | 0.400 | 28 | 52 |
| | 0.00150 | 0 | 0.200 | 8 | 41 |
| (b) OCOCH$_3$ | 0.000750 | 0 | 0.400 | 28 | 44 |
| | 0.000750 | 0 | 0.200 | 8 | 23 |
| (a) 4-methylcyclohexyl 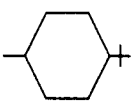 | 0.250 | 17 | 0.400 | 22 | 60 |
| | 0.250 | 17 | 0.200 | 19 | 48 |
| (b) Cl | 0.125 | 14 | 0.400 | 22 | 68 |
| | 0.125 | 14 | 0.200 | 19 | 34 |
| (a) 1,1-dimethylcyclohexyl 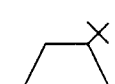 | 0.100 | 24 | 0.400 | 21 | 60 |
| | 0.100 | 24 | 0.200 | 26 | 47 |
| (b) OH | 0.0500 | 8 | 0.400 | 21 | 51 |
| | 0.0500 | 8 | 0.200 | 26 | 35 |

TABLE III-continued

Naphthoquinone alone with structure: naphthalene-1,4-dione with R¹ and R² substituents at 2,3 positions.

(a) R¹
(b) R²

| (a)/(b) group | Concentration in mg/L | % Inhibition | Clopidol (4-pyridinol) alone Concentration in mg/L | % Inhibition | Naphthoquinone + Clopidol (4-pyridinol) % Inhibition |
|---|---|---|---|---|---|
| (a) cyclopentyl | 1.25 | 2 | 0.400 | 21 | 67 |
|  | 1.25 | 2 | 0.200 | 25 | 65 |
| (b) OH | 0.625 | 0 | 0.400 | 21 | 52 |
|  | 0.625 | 0 | 0.200 | 25 | 27 |
| (a) (CH₂)₃-cyclohexyl | 0.0500 | 22 | 0.400 | 18 | 59 |
|  | 0.0500 | 22 | 0.200 | 14 | 65 |
| (b) OH | 0.0250 | 19 | 0.400 | 18 | 61 |
|  | 0.0250 | 19 | 0.200 | 14 | 37 |
| (a) t-butylcyclohexyl | 0.0000125 | 13 | 0.400 | 14 | 47 |
|  | 0.0000125 | 13 | 0.200 | 5 | 36 |
| (b) OH | 0.00000625 | 17 | 0.400 | 14 | 51 |
|  | 0.00000625 | 17 | 0.200 | 5 | 21 |
| (a) 4-(3,4-dimethylphenyl)cyclohexyl | 0.00025 | 30 | 0.200 | 16 | 55 |
|  | 0.00025 | 30 | 0.100 | 0.4 | 48 |
| (b) OH | 0.000125 | 15 | 0.200 | 16 | 60 |
|  | 0.000125 | 15 | 0.100 | 0.4 | 38 |
| (a) (CH₂)₁₂Me | 0.0156 | 10 | 0.200 | 10 | 42 |
|  | 0.0156 | 10 | 0.100 | 10 | 28 |
| (b) OH | 0.0078 | 4 | 0.200 | 10 | 36 |
|  | 0.0078 | 4 | 0.100 | 10 | 26 |

EXAMPLE 3

Effect of 4-pyridinol analogue/2-(4-t-butylcyclohexyl)-3-hydroxy-1,4-naphthoquinone combinations on *P.falciparum*

By the method of Example 1 the effect of a number of 2-(4-t-butylcyclohexyl)-3-hydroxy-1,4-naphthoquinone/4-pyridinol analogue combinations on *P.falciparum* in vitro were determined. Results, expressed as % inhibition of radioactivity incorporation, are given in Table IV.

TABLE IV

Naphthoquinone alone: 2-(4-t-butylcyclohexyl)-3-hydroxy-1,4-naphthoquinone 4-pyridinol analogue alone: pyridine with X substituents at 3,5 positions and R³ at 2,6 positions.

| Naphthoquinone alone | | 4-pyridinol analogue alone | | | Naphthoquinone + 4-pyridinol analogue |
|---|---|---|---|---|---|
| Concentration in mg/L | % Inhibition | X | R³ | Concentration in mg/L | % Inhibition | % Inhibition |
| 0.0000625 | 7 | Br | Me | 0.25 | 14 | 40 |
| 0.00003125 | 5 | | | 0.25 | 14 | 27 |
| 0.0000625 | 7 | | | 0.125 | 2 | 30 |
| 0.00003125 | 5 | | | 0.125 | 2 | 16 |
| 0.0000625 | 19 | Cl | Pr | 1.25 | 24 | 58 |
| 0.00003125 | 2 | | | 1.25 | 24 | 36 |

TABLE IV-continued

Naphthoquinone alone / 4-pyridinol analogue alone / Naphthoquinone + 4-pyridinol analogue

| Concentration in mg/L | % Inhibition | X | R³ | Concentration in mg/L | % Inhibition | % Inhibition |
|---|---|---|---|---|---|---|
| 0.0000625 | 19 | | | 0.625 | 12 | 48 |
| 0.0000325 | 2 | | | 0.625 | 12 | 38 |
| 0.0000625 | 22 | Br | Pr | 6.25 | 15 | 78 |
| 0.0000156 | 0.5 | | | 6.25 | 15 | 25 |
| 0.0000625 | 22 | | | 3.125 | 9 | 59 |
| 0.0000156 | 0.5 | | | 3.125 | 9 | 27 |

EXAMPLE 4

Effect of combinations of 2-(4-cyclohexylcyclohexyl)-3-hydroxy-1,4-naphthoquinone and 3,5-dichloro-2,6-dimethylpyridinol on *P.yoelii* in vivo.

The naphthoquinone and the pyridinol were each suspended in 0.25% (w/v) celacol in water by milling for 16–24 hours at 26° C. The suspensions were subsequently serially diluted with 0.25% (w/v) celacol in water.

At time 0, 0.1 ml of a suspension of $10^7$ *P.yoelii*-parasitised red blood cells/ml of phosphate buffered saline were injected intravenously into 15–20 g mice through a tail vein. Groups of 5 mice per treatment were dosed orally at times 6, 22, 30, 46, 54, 70 and 78 hours with 0.2 ml of the drug suspension. Tail-blood smears were taken at 96 hours, stained with Giemsa and the percentage of red blood cells infected determined and compared to untreated, infected controls. Percent inhibition was correlated with dose to provide $ED_{50}$ values for each drug alone.

In subsequent experiments dilutions of the two drugs, alone and in combination were used, and the percentage inhibition of parasitaemia and $ED_{50}$ values (of each drug at fixed concentrations of the other) were determined.

The results are shown respectively in Tables V and VI.

TABLE V

| Concentrations of naphthoquinone mg/Kg/dose | Concentration of Clopidol (4-pyridinol) in mg/Kg/dose | | | | | |
|---|---|---|---|---|---|---|
| | 0.0 | 30 | 15 | 7.5 | 3.7 | 1.9 | 0.94 |
| 0.0 | 0 | 61 | 34 | 13 | 17 | 6 | |
| 0.60 | 99 | | | | | | |
| 0.30 | 74 | | | | | 98 | 96 |
| 0.15 | 16 | | | | 92 | 80 | 62 |
| 0.075 | 17 | | | 86 | 69 | 45 | 35 |
| 0.037 | 28 | | 77 | 73 | 32 | 23 | 20 |
| 0.019 | 13 | | 48 | 42 | 11 | 23 | 16 |

TABLE VI

| Fixed concentration of Clopidol (4-pyridinol) in mg/kg/dose | $ED_{50}$ for naphthoquinone in mg/Kg/dose | Fixed concentration of naphthoquinone | $ED_{50}$ for Clopidol (4-pyridinol) in mg/Kg/dose |
|---|---|---|---|
| 0.000 | 0.224 (0.224 to 0.208) | 0.000 | 22.5 (27.6 to 19.4) |
| 0.94 | 0.109 (0.125 to 0.0909) | 0.019 | 13.8 (21.5 to 10.7) |
| 1.9 | 0.0762 (0.0975 to 0.0599) | 0.0375 | 5.14 (6.22 to 4.23) |
| 3.75 | 0.0519 (0.0599 to 0.0450) | 0.075 | 1.87 (2.45 to 1.30) |
| 7.5 | 0.0219 (0.0274 to 0.0151) | 0.15 | 0.522 (0.946 to 0.0356) |
| 15. | 0.0197 (0.0242 to 0.0121) | | |

EXAMPLE 5

Effect of Naphthoquinone clopidol (4-pyridinol) Combinations on *P.yoelii* in vivo A number of combinations of clopidol (4-pyridinol) and naphthoquinones were assayed and compared with each drug alone for their antimalarial effect against *P.yoelii* in vivo by the method of Example 4. Representative results for each combination showing percentage inhibition of parasitaemia are given in Table VII below.

TABLE VII

Naphthoquinone alone (a) $R^1$
(b) $R^2$

| | Naphthoquinone alone Concentration in mg/Kg × 7 | % Inhibition | Clopidol (4-pyridinol) alone Concentration in mg/Kg × 7 | % Inhibition | Naphthoquinone and Clopidol (4-pyridinol) in combination % Inhibition |
|---|---|---|---|---|---|
| (a) −(CH₂)₈−cyclohexyl | 1.0 | 19 | 5.0 | 0 | 55 |
| | 1.0 | 19 | 2.5 | 0 | 31 |
| (b) OH | 0.50 | 7 | 5.0 | 0 | 45 |
| | 0.50 | 7 | 2.5 | 0 | 10 |
| (a) cyclohexyl | 3.0 | 15 | 3.75 | 0 | 97 |
| | 3.0 | 15 | 1.9 | 0 | 64 |
| (b) OH | 1.5 | 1 | 3.75 | 0 | 76 |
| | 1.5 | 1 | 1.9 | 0 | 47 |
| (a) bicyclohexyl | 0.15 | 16 | 3.75 | 16 | 92 |
| | 0.15 | 16 | 1.9 | 6 | 80 |
| (b) OH | 0.075 | 17 | 3.75 | 16 | 69 |
| | 0.075 | 17 | 1.9 | 6 | 45 |
| (a) cyclohexyl-phenyl | 0.050 | 0 | 3.75 | 16 | 73 |
| | 0.050 | 0 | 1.9 | 0 | 34 |
| (b) OH | 0.040 | 0 | 3.75 | 16 | 39 |
| | 0.040 | 0 | 1.9 | 0 | 23 |
| (a) CH₂−cyclohexyl-t-Bu | 1.0 | 19 | 4.3 | 14 | 93 |
| | 1.0 | 19 | 1.4 | 2 | 52 |
| (b) OH | 0.50 | 10 | 4.3 | 14 | 61 |
| | 0.50 | 10 | 1.4 | 2 | 17 |
| (a) cyclohexyl-(Et)₂ | 1.0 | 4 | 4.3 | 14 | 75 |
| | 1.0 | 4 | 1.4 | 2 | 68 |
| (b) OH | 0.50 | 5 | 4.3 | 14 | 54 |
| | 0.50 | 5 | 1.4 | 2 | 14 |
| (a) cyclohexyl-(4-Cl-phenyl) | 0.020 | 12 | 4.3 | 7 | 90 |
| | 0.020 | 12 | 1.4 | 4 | 55 |
| (b) OH | 0.010 | 5 | 4.3 | 7 | 68 |
| | 0.010 | 5 | 1.4 | 4 | 29 |
| (a) cyclohexyl-O-t-Bu | 0.25 | 5 | 4.3 | 7 | 97 |
| | 0.25 | 5 | 13 | 5 | 80 |
| (b) OH | 0.13 | 1 | 4.3 | 7 | 84 |
| | 0.13 | 1 | 13 | 5 | 31 |

TABLE VII-continued

Naphthoquinone alone structure: 1,4-naphthoquinone with R¹ at 2-position and R² at 3-position

| (a) R¹ / (b) R² | Concentration in mg/Kg × 7 | % Inhibition | Clopidol (4-pyridinol) alone Concentration in mg/Kg × 7 | % Inhibition | Naphthoquinone and Clopidol (4-pyridinol) in combination % Inhibition |
|---|---|---|---|---|---|
| (a) cyclohexyl | 5.0 | 3 | 4.3 | 1 | 86 |
|  | 5.0 | 3 | 1.4 | 0 | 22 |
| (b) OCOCH₃ | 2.5 | 2 | 4.3 | 1 | 50 |
|  | 2.5 | 2 | 1.4 | 0 | 3 |
| (a) gem-dimethylcyclohexyl | 5.0 | 0 | 4.3 | 1 | 73 |
|  | 5.0 | 0 | 1.4 | 0 | 46 |
| (b) OH | 2.5 | 0 | 4.3 | 1 | 45 |
|  | 2.5 | 0 | 1.4 | 0 | 22 |
| (a) (CH₂)₈Me | 9.0 | 69 | 4.3 | 0 | 99 |
|  | 9.0 | 69 | 1.4 | 0 | 88 |
| (b) OH | 3.0 | 3 | 4.3 | 1 | 76 |
|  | 3.0 | 3 | 1.4 | 1 | 42 |
| (a) t-butylcyclohexyl | 0.9 | 35 | 5.0 | 1 | 97 |
|  | 0.9 | 35 | 2.5 | 0 | 96 |
| (b) OH | 0.6 | 24 | 5.0 | 1 | 94 |
|  | 0.6 | 24 | 2.5 | 0 | 74 |

EXAMPLE 6—Toxocity

The acute oral $LD_{50}$'s of compounds of formula (I) in rats were determined by standard techniques. The results are shown below.

| Compound | $LD_{50}$ |
|---|---|
| 2-(4'-t-butylcyclohexyl)-3-hydroxy-1,4 naphthoquinone | >1000 mg/kg bodyweight |
| 2-hydroxy-3-(4'-t-pentylcyclohexyl)-1,4-naphthoquinone | 2000 mg/kg bodyweight |

EXAMPLE 7

The following examples illustrate therapeutic formulations according to the invention wherein the combination is a combination herein described, specifically a combination of 2-(4-t-butylcyclohexyl)-3-hydroxy-1,4-naphthoquinone and 3,5-dichloro-2,6-dimethylpyridinol.

| Tablet formulation | |
|---|---|
| Combination | 100 mg |
| Lactose | 100 mg |
| Maize starch | 30 mg |
| Magnesium stearate | 2 mg |
| | 232 mg |

| Oral suspension | |
|---|---|
| Combination | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

| Injectable suspension | |
|---|---|
| Combination | 100 mg |
| Polyvinyl pyrrolidine (RVP) | 170 mg |
| Tween 80 | 0.2% v/v |
| Methylhydroxybenzoate | 0.1% w/v |
| Water for injection | to 3 ml |

| Capsule | |
|---|---|
| Combination | 100 mg |
| Starch 1500 | 150 mg |
| Magnesium stearate | 2.5 mg |
| filled into a soft gelatin capsule | |

We claim:

1. An antimalarial composition comprising an amount of a first compound 2-[4-(4-chlorophenyl)cyclohexyl]-3-hydroxy-1,4-naphthoquinone and a second compound 3,5-dichloro-2,6-dimethylpyridinol the first and second compounds being present in an amount to provide a synergistic combination.

2. A method for treating or preventing maliaria in an animal, which comprises the administration of an effective antimaliarial amount of the composition of claim 1 to said animal.

* * * * *